(12) United States Patent
Lai et al.

(10) Patent No.: US 9,163,214 B2
(45) Date of Patent: Oct. 20, 2015

(54) METHOD FOR CULTURING STEM CELLS

(75) Inventors: Dongmei Lai, Shanghai (CN); Weiwei Cheng, Shanghai (CN); Lihe Guo, Shanghai (CN); Tianjin Liu, Shanghai (CN); Lizhen Jiang, Shanghai (CN); Qin Huang, Shanghai (CN)

(73) Assignees: SHANGHAI ICELL BIOTECHNOLOGY CO., LTD., Shanghai (CN); SHANGHAI UNITED STEM CELL BIOTECHNOLOGY CO., LTD., Shanghai (CN); INTERNATIONAL PEACE MATERNITY HOSPITAL, Shanghai (CN)

( * ) Notice: Subject to any disclaimer, the term of this patent is extended or adjusted under 35 U.S.C. 154(b) by 815 days.

(21) Appl. No.: 13/379,651

(22) PCT Filed: May 4, 2010

(86) PCT No.: PCT/CN2010/000616
§ 371 (c)(1),
(2), (4) Date: Dec. 20, 2011

(87) PCT Pub. No.: WO2010/127555
PCT Pub. Date: Nov. 11, 2010

(65) Prior Publication Data
US 2012/0122213 A1 May 17, 2012

(30) Foreign Application Priority Data
May 5, 2009 (CN) .......................... 2009 1 0050582

(51) Int. Cl.
*C12N 5/0735* (2010.01)
*C12N 5/074* (2010.01)
*C12N 5/095* (2010.01)

(52) U.S. Cl.
CPC ............ *C12N 5/0606* (2013.01); *C12N 5/0607* (2013.01); *C12N 2501/115* (2013.01); *C12N 2501/235* (2013.01); *C12N 2502/025* (2013.01)

(58) Field of Classification Search
CPC ............. C12N 5/0605; C12N 2533/90; C12N 2502/02; C12N 5/0607; C12N 2500/99; C12N 2501/235; C12N 2502/025; C12N 5/0606; C12N 2501/115
USPC .................................. 435/371, 373, 325, 366
See application file for complete search history.

(56) References Cited

PUBLICATIONS

Lai et al. Use of Human Amnion Epithelial Cells as a Feeder Layer to Support Undifferentiated Growth of Mouse Embryonic Stem Cells. Cloning and Stem Cells vol. 11, No. 2, 2009. p. 331-340.*
Takahashi et al. Induction of Pluripotent Stem Cells from Adult Human Fibroblasts by Defined Factors. Cell 131, 861-872, Nov. 30, 2007.*

* cited by examiner

*Primary Examiner* — Taeyoon Kim
(74) *Attorney, Agent, or Firm* — Perkins Coie LLP

(57) ABSTRACT

In the field of biological technology, a stem cell culture method is provided. The method includes preparing an amniotic epithelial cell feeder layer that is not treated to lose the division ability; and seeding the stem cells onto the amniotic epithelial cell feeder layer, and culturing in a culture medium. The stem cell culture method according to the present invention does not require the treatment of the feeder layer cells to lose the division ability, and is thus simple and safe, thereby effectively solving the problem of contamination caused by animal-derived ingredients in culture of human stem cells at present, greatly reducing the culture cost of the stem cells, and providing a safe, effective, and inexpensive stem cell culture method for the industrialization of the stem cells in the future.

12 Claims, 5 Drawing Sheets

METHOD FOR CULTURING STEM CELLS

BACKGROUND

1. Technical Field

The present invention relates to the filed of biological technology, and more particularly to a stem cell culture method.

2. Related Art

Stem cells are a class of self-renewing pluripotent cells, which are able to be differentiated into many different functional cells under certain conditions. The stem cells may be classified by two methods. In a first method, the stem cells are classified into embryonic stem cells (ES cells) and somatic stem cells according to the development stage of the stem cells. In a second method, the stem cells are classified into totipotent stem cells (TSCs), pluripotent stem cells, and unipotent stem cells according to the development potential of the stem cells.

ES cells are mainly derived from inner cell mass (ICM) of a blastocyst and early embryonic cells before a fertilized ovum is developed into a morula. Human ES cells have 2 distinguished features, one is the high in-vitro self-renewing ability, and the second one is the ability to be differentiated into various types of cells in human body by directed induction.

Induced pluripotent stem cells (also referred to as iPSs) are ES cell-like pluripotent cells obtained by directly reprogramming animal or human somatic cells by introducing some factors into the somatic cells through gene transfection technology. This type of cells are very similar to the ES cells, as far as the cell morphology, growth characteristics, surface markers, and teratoma formation are concerned (Okita K, Ichisaka T, Yamanaka S. Nature 2007; 448: 313-317; Wernig M, Meissner A, et al. Nature 2007; 448: 318-324; Takahashi K, Tanabe K, Ohnuki M, et al. Cell 2007; 131: 861-872; and Yu J, Vodyanik M A, Smuga-Otto K, et al. Science 2007; 318: 1917-1920).

Somatic stem cells include stem cells found in adult tissues, such as bone marrow, umbilical cord or peripheral blood hematopoietic stem cells, bone marrow or umbilical cord mesenchymal stem cells, epidermal stem cells, adipose-derived stem cells, pancreatic stem cells, and neural stem cells, and can be theoretically differentiated into specific tissues and organs under specific conditions, thus being a foundation for repair and regeneration.

The stem cells have a wide application prospect in medicine. However, if the stem cells are intended to be successfully used in clinical practice, how to maintain the stem cells in an undifferentiated state while the stem cells proliferate in vitro, i.e., self renewal, is a first subject needed to be solved. The in-vitro culture of the stem cells requires 2 basic conditions, that is, the differentiation of the cells is inhibited while the division and proliferation of the cells are facilitated. In an existing stem cell culture technology, feeder layer cells and/or cell factors are generally used to meet the above conditions. For the ES cells, the commonly used feeder layer cells include, for example, murine embryonic fibroblasts (MEFs) and STO cells, which lose the division ability after, for example, irradiation with γ ray or treatment with mitomycin C. The cells can still survive and have the ability to assimilate the culture medium while losing the division ability. Use of the MEFs as the feeder layer to culture the ES cells is the earliest and most commonly used method [Takahama Y, Ochiya T, Sasaki H, et al. J. Oncogene, 1998, 16(24):3189-3196]; and the culture medium is also supplemented with cell differentiation inhibitors such as leukemia inhibitory factor (LIF) [Horak V, Flechon J E. Reprod Nutr Dev, 1998, 38(6): 683-695]. However, the disadvantages in use of the MEFs to culture the ES cells are that (1) in culturing and expanding the human ES cells, the MEFs may spread animal pathogens to the human ES cells through the culture medium; and (2) a large amount of MEFs need to be produced, since the MEFs have a limited life cycle, cannot be passaged in vitro for a long period of time, and have an ability of generating the proliferation factor and the differentiation inhibitor that is diminished or even lost with the extension of the passage time; (3) it is difficult to obtain pure ES cells for biochemical and molecular biological analysis; and (4) the release of the chromosome from dead MEFs may cause the mutation of the ES cells and affects the maintenance of normal karyotype. In view of the problems brought by use of the MEFs in clinical, some scholars establish a culture medium with human source embryonic or somatic cells as the feeder cell and without animal-derived ingredients. The long-term undifferentiated proliferation state of the human ES cells can be maintained by respectively using human embryonic fibroblasts (HEFs), adult oviductal epithelial cells, human bone marrow stromal cells, or human foreskin cells as the feeder layer in place of the MEFs [Richards M, Fong C Y, Chan W K, et al. Nat Biotechnol, 2002, 20 (9):933-936; Cheng L, Hammond H, Ye Z, et al. Stem Cells, 2003, 21(2):131-142; and Meng G, Liu S, Krawetz R, et al. Stem Cells Dev. 2008, 17(3):413-22]. However, the culture system based on human feeder layer still requires the feeder layer cells and the ES cells to grow at the same time, and the human tissues cannot meet the demand for in-vitro culture and expansion of the ES cells due to the difficulty exiting in obtaining of the human tissues. In order to solve the difficulty exiting in obtaining of the human tissues, human placenta tissue is used and cells are isolated therefrom to culture embryonic stem cells. Genbacev et al [Genbacev O., Krtolica A., Zdravkovic T., et al. Fertil Steril 2005, 83, 1517-1529.] isolate human placenta fibroblasts from aborted pregnancy tissue of 6-9 weeks, and find that the human placenta fibroblasts can support the growth of the human embryonic stem cells and keep them in the undifferentiated state. However, the treatment through which the feeder layer cells lose the division ability, for example, irradiation with γ ray or treatment with mitomycin C, increases not only the operation steps, but also potential risks, because mitomycin C is a DNA inhibitor, which may cause the chromosome deformity of the ES cells.

For this reason, in order to overcome the problem of contamination caused by animal-derived ingredients, attempts are made to use a serum-free and feeder layer-free system to culture the stem cells, in which various growth factors are supplemented to ensure that the stem cells are maintained in the undifferentiated sate while continuously proliferating in vitro. However, the growth factors and the culture medium containing the same are very expensive, thereby increase the research and application cost.

SUMMARY

In view of the technical problems above, the present invention is directed to a safe, effective, and inexpensive stem cell culture method, so as to overcome the disadvantages existing in the stem cell culture method in the prior art.

The present invention provides a stem cell culture method, which includes:

a) preparing an amniotic epithelial cell feeder layer that is not treated to lose the division ability; and b) seeding the stem cells onto the amniotic epithelial cell feeder layer, and culturing in a culture medium.

In the present invention, the step of preparing the amniotic epithelial cell feeder layer that is not treated to lose the division ability is peeling off the amnion from the placenta obtained after parturition through cesarean section, isolating amniotic epithelial cells, seeding the amniotic epithelial cells into a cell culture container, and culturing in a cell incubator at 37° C. with 5% $CO_2$.

In a preferred embodiment, the amniotic epithelial cells are mammalian amniotic epithelial cells.

In a preferred embodiment, the amniotic epithelial cells are human amniotic epithelial cells, so as to avoid the contamination caused by animal-derived ingredients in culture of human-derived stem cells.

In a preferred embodiment, the amniotic epithelial cells are amniotic epithelial cells of passages $P_0$-$P_3$, with the amniotic epithelial cells of passage $P_0$ being preferred.

In a preferred embodiment, the stem cell may be embryonic stem cells, embryonic germ cells, iPS cells, or somatic stem cells, with the embryonic stem cells, embryonic germ cells, or iPS cells being preferred.

In a preferred embodiment, the embryonic stem cells or iPS cells are human embryonic stem cells or human iPS cells.

In a preferred embodiment, if the stem cells are embryonic stem cells and/or iPS cells, the concentration of LIF in the culture medium is 0-12 ng/ml and preferably 0 ng/ml, so as to avoid the potential risk caused by supplementation of the LIF and decrease the culture cost.

In a preferred embodiment, the culture medium may be a serum-free culture medium or a serum-containing culture medium, in which the serum is preferably human whole serum, or umbilical cord serum.

The stem cell culture method according to the present invention does not require the treatment of the feeder layer cells to lose the division ability, and is thus simple and safe, thereby effectively solving the problem of contamination caused by animal-derived ingredients in culture of human stem cells at present, greatly reducing the culture cost of the stem cells, and providing a safe, effective, and inexpensive stem cell culture method for the industrialization of the stem cells in the future.

BRIEF DESCRIPTION OF THE DRAWINGS

The present disclosure will become more fully understood from the detailed description given herein below for illustration only, and thus are not limitative of the present disclosure, and wherein.

DETAILED DESCRIPTION

Figure 1A:
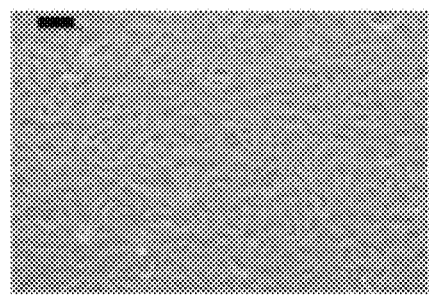
FIGS. 1A-D show growth of human embryonic stem cell line hHES1 on HAEC and MEF feeder layers.

To further describe the conventional techniques used in practice of the present invention in detail, a practitioner may make reference to standard textbooks and reviews regarding cell biology, histology, and embryology, including Teratocarcinomas and embryonic stem cell: A practical approach [edited by E. J. Robertson, IRL Press Ltd., 1987]; Guide to techniques in Mouse Development [edited by P. M. Wasserman et al., Academic Press, 1993]; Embryonic Stem Cell Differentiation in Vitro [M. V. Wiles, Meth. Enzymol. 225: 900, 1993]; Properties and uses of Embryonic Stem Cells: Prospects for Application to Human Biology and Gene Therapy [P. D. Rathjen et al., Reprod. Fertil. Dev. 10: 31, 1998].

Cell biology, protein chemistry, and antibody technique can be found in "Current Protocols in Protein Science" [edited by J. E. Colligan et al., Wiley & Sons], "Current Protocols in Cell Biology" [edited by J. S. Bonifacino et al., Wiley & Sons], and "Current protocols in Immunology" [edited by J. E. Colligan et al., Wiley & Sons]. Reagents, cloning vectors, and gene operation kits involved in the present invention may be available from commercial providers, for example, Bio-Rad, Stratagene, Invitrogen, ClonTech, and Sigma-Aldrich Co.

Cell culture methods are generally described in "Culture of Animal Cells: A Manual of Basic Technique", latest version (edited by R. I. Freshney, Wiley & Sons); "General Techniques of Cell Culture" (edited by M. A. Harrison and I. F. Rae, Cambridge University Press); and "Embryonic Stem Cells, Methods and Protocols" (edited by K. Turksen, Humana press). The tissue culture media and reagents can be available from the commercial providers, for example, Gibco/BRL, Nalgene-Nunc International, Sigma Chemical Co., and ICN Biomedicals.

Term "treatment through which the division ability is lost" as used herein refers to a process in which by using the physical or chemical means, such as irradiation with γ ray or treatment with mitomycin C, the cells can still survive and have the ability to assimilate the culture medium while losing the division ability.

Treatment of Amnion Tissue Sample

Amnion was separated from ex-vivo mammalian placenta, washed with a physiological buffer to remove blood cells, and then mechanically picked off the remaining chorion and blood vessel.

Term "mammalian" as used herein is the most advanced group of animals in the vertebrate, which is evolved from reptiles, and has the following main features. The mammalian has fur on surface thereof, is generally divided into five parts including head, neck, body, extremity, and tail, breaths with lung, has a constant body temperature and is thus a homoiothermal animal, has a big and well-developed brain, and is breastfeeding and viviparous. Breastfeeding and viviparity are the most distinguished features of the mammalian.

Term "amnion" as used herein is also referred to as fetal membrane, which is an important tissue for exchanging materials between mother and fetus. Amnion mainly includes five parts, i.e. epithelial layer, basal layer, compact layer, fibroblast layer, and spongy layer. Human amniotic cells are mainly formed by the human amniotic epithelial cells (hAECs) in the epithelial layer and the mesenchymal cells in the basal layer, and are early embryonic development products which are closely related to the developing fetus. The amniotic epithelial cells can express, for example, some different molecular markers of the embryonic stem cells and some early stem cells, such as Oct4, Nanog, SOX-2, SSEA-3, and SSEA-4; neural cell specific glial fibrillary associated proteins, neuron-specific marker (MAP2), and neural stem cell specific marker (Nestin); and liver parenchyma cell protein, and alpha fetoprotein. This suggests that the amnion has pluripotent differentiation potential since the amnion keeps the embryo-like immature low-differentiation cell feature [Knezevic V, Anat 1996; 189 (Pt 1): 1-7; Yugel, Transplantation 2004; 77(9): 1452-4; Takashima S, Cell Struct Funct 2004; 29(3): 73-84; Sakuragawa N, Neurosci Lett 1996; 209 (1): 9-12; and Wei J. P, Cell Transplant 2003; 12(5): 545-52]. Meanwhile, the amniotic cells are deficient of the type I and II antigens such as HLA-A, -B, -C and -R antigens and β2 immunoglobulin [Akle C A, Lance 1981; 2 (8254): 1003-5; and M. Adinolfi, Nature 295: 28], and thus no immunogenicity is generated after transplant. In addition, the amniotic cells have HLA-E and -G antigens which are immunosuppressive [Ueta M et al., Clin Exp Immunol 2002; 129 (3): 464-70].

Isolation and Culture of Amniotic Epithelial Cells

"Isolation" refers to removal of cells from a tissue sample and separation of the cells from other non-tissue stem cells. An intact tissue was separated into single cells by using any conventional techniques and methods including mechanical force (cutting force or shearing force), enzymatic digest by sing one or combined proteases such as collagenase, trypsase, and lipase, for example, the liberase H1 disclosed in U.S. Pat. No. 5,952,215 and pepsin, or a combination of mechanical and enzymatic methods. For example, an intact tissue section could be digested by a collagenase mediated tissue digestion method, or with reference to other methods using the collagenase disclosed in U.S. Pat. Nos. 5,830,714 and 5,952,215 and cited in the present invention. Similarly, a neutral protease might be used in place of the collagenase as described in, for example, the method publicized in Twentyman, P. R. and J. M. Yuhas (Cancer Lett 1980: 9 (3): 225-228). Moreover, in a method, a combination of enzymes might be used, for example, the combination of collagenase and trypsin, as described in, for example, the method publicized in Russell, S. W. F. Doc et al. (Int J Cancer 1976: 18 (3): 322-30); or a combination of an enzyme such as trypsin and mechanical disassociation might be used as described in, for example, the method publicized in Engelholm. S. A, M. Spang. Thomsen et al. (Br J Cancer 1985: 51 (1): 93-98).

The living cell populations were concentrated by methods known to those skilled in the art. The post-treatment washing and concentration steps might be performed separately or simultaneously. In an implementation, the cells were concentrated and the enzyme was removed by flowing the cell populations continuously through a rotary membrane system or a similar system such as that disclosed in U.S. Pat. Nos. 034, 135 and 5,234,608.

In addition to the above method, the living cell populations might be further purified and enriched after the cells were washed and cultured, so as to reduce the non-amniotic epithelial cells and dead cells. The separation of the cells from a suspension might be achieved by buoyant density sedimentation and centrifugation, differential adhesion to a solid phase and eluting from the solid phase, immunomagnetic beads, Fluorescence-activated cell sorting (FACS) or other technologies. Examples for the different technologies and the apparatus for implementing the technologies might be made reference to those described in the prior art and commercially available products. Taking the immunomagnetic beads as an example, directed to the amniotic epithelial cell antigen disclosed in WO03042405, specific antibodies such as SSEA-4, Nanog, and CK-3 were used, and amniotic epithelial cells with SSEA-4(+), Nanog(+), and CK-3(+) were further purified or enriched by immunomagnetic beads.

The types of basic culture media used in the present invention were not limited, as long as they were those that could be used for cell culture. The preferred culture media included DMEM and NPBM. The types of other ingredients that might be contained in the basic culture media were not limited, and preferred ingredients included F-12, FCS and nerve growth factor. In the culture medium, the concentrations of F-12 and FCS were, for example, 50% and 10% respectively. In the culture medium, the concentration of $CO_2$ was preferably 5%, but the present invention was not limited thereto.

Moreover, in another preferred implementation of the present invention, basic fibroblast growth factors (bFGF) or epidermal growth factor (EGF) were added to the basic culture media. In this case, either one or both of them might be added. The concentration of bFGF or EGF was, for example, 1 ng/ml to 100 ng/ml, and preferably 10 ng/ml. The addition time and manner were not limited. Preferably, the agents were added to the basic culture media every day in culture of the amniotic epithelial cells.

Based on the present invention, human whole serum, umbilical cord serum, animal serum, animal embryonic serum, or artificial cerebrospinal fluid (ACSF) might be further added to the basic culture media or the basic culture media containing other ingredients.

Source and Culture of Stem Cells

Various types of stem cells might be used in the present invention, and unless indicated otherwise, the stem cells derived from any vertebrate could be used in the present invention, including, but not limited to, embryonic stem cells (ES cells), induced pluripotent stem cells (also referred to as iPSs), embryonic germ (EG) cells, and somatic stem cells.

The ES cells might be derived from a blastocyst of a primate [Thomson et al., Proc. Natl. Acad. Sci. USA 92: 7844, 1995]. For example, human embryonic stem (hES) cells could be derived from human blastocyst cells by using the technology described by Thomson et al. [U.S. Pat. No. 5,843, 780, Science 282:1145, 1998] or the technology described by Reubinoff et al. [Nature Biotech. 18: 399, 2000].

Embryonic germ (EG) cells such as human embryonic germ (hEG) cells could be derived from primordial germ cells (which were found in fetal material of about 8-11 weeks after the last menstrual period). The descriptions for suitable preparation methods might be made reference to Shamblott et al., Proc. Natl. Acad. Sci. USA 95: 13726, 1998 and U.S. Pat. No. 6,090,622.

Induced pluripotent stem cells (also referred to as iPS cells) are ES cell-like pluripotent cells obtained by directly reprogramming animal or human somatic cells by introducing some factors into the somatic cells through gene transfection technology. The preparation and culture of the iPS cells might be made reference to Okita K, Ichisaka T, Yamanaka S. Nature 2007; 448: 313-317; Wernig M, Meissner A, et al. Nature 2007; 448: 318-324; Takahashi K, Tanabe K, Ohnuki M, et al. Cell 2007; 131: 861-872; and Yu J, Vodyanik M A, Smuga-Otto K, et al. Science 2007; 318: 1917-1920.

Somatic stem cells include stem cells found in adult tissues, such as bone marrow or umbilical cord mesenchymal stem cells, pancreatic stem cells, neural stem cells, epidermal stem cells, adipose-derived stem cells, and neural stem cells, or bone marrow, umbilical cord or peripheral blood hematopoietic stem cells, which include the following non-limitative embodiments. U.S. Pat. No. 5,851,832 reports the pluripotent neural stem cells derived from brain tissue; U.S. Pat. No. 5,766,948 reports the neuron cells produced in brain hemispheres of neonates; U.S. Pat. Nos. 5,654,183 and 5,849,553 report the use of the mammalian Neural crest stem cells; and WO2009040458 discloses a method for preparing blood pluripotent mesenchymal stem cells.

Unless otherwise defined, all professional and scientific terms used herein have the same meaning as those familiar to persons of skill in the art. In addition, any method and material similar or equivalent to those described can be used in the method of the present invention. The present invention is further described below with reference to specific embodiments. The embodiments are only used to illustrate the present invention, instead of limiting the scope of the present invention. In test methods without specific conditions in the embodiments, the routine conditions or the conditions recommended by manufacturers are generally used.

Embodiment 1. Preparation of Human Amniotic Epithelial Cell Feeder Layer

Isolation and culture of human amniotic epithelia cells (HAECs): the amnion was peeled off from the placenta (which was negative for various virus indication, including types A, B, C, and E hepatitis, HIV, and syphilis) obtained after parturition through cesarean section, the amniotic epithelial cells were isolated, washed with PBS to remove the blood cells, digested with 0.25% trypsin at 37° C. for 30 min, beaten, added with RPMI1640 containing 10% of human umbilical cord serum to quench the digest, filtered with a sieve of 100 meshes, and centrifuged at 1,500 rpm. The supernatant was discarded, and the cells were inoculated at $1 \times 10^4$/$cm^2$ in a 10 cm petri dish, and cultured in a cell incubator at 37° C. with 5% $CO_2$ to 80% confluence.

Embodiment 2. Preparation of Mouse Embryonic Fibroblast (MEF) Feeder Layer

Isolation and culture of mouse embryonic fibroblasts (MEFs): embryos of mice during pregnancy at day 12.5 were removed of the viscera, head, and tail, and washed two times with PBS. The tissue was scissored, digested with 0.25% trypsin for 30 min, beaten uniformly with a burette, and centrifuged at 1000 rpm for 5 min The supernatant was discarded, and the cell pellets were beaten uniformly, added with DMEM culture medium (containing 10% FBS), cultured in an incubator at 37° C. with 5% $CO_2$, and treated with mitomycin C after 2-3 passages.

Embodiment 3. Culture of Human Embryonic Stem Cells

The human embryonic stem cell line hHES1 was respectively cultured on the two feeder layers obtained in Embodiments 1 and 2 [Wu C F, Tsung H C, Zhang W J, et al. Reprod Biomed Online. 2005 December; 11(6):733-9]. KO-DMEM medium supplemented with 10 ng/ml bFGF, 5% human umbilical cord serum, and 12 ng/ml hLIF was used, HES cell clones at day 3 day of culture were used for molecular biological test, and qRealtime-PCR, immunofluorescence IF, and Western blotting were used for detecting the gene expression differences of Nanog, Oct4 and other markers; and flow cytometry (FCM) was used for detecting the cell cycle difference of HES. hHES1 after 20 passages was analyzed for chromosome karyotype by G banding. $1 \times 10^6$ HES cells was collected and intramuscularly injected respectively into the back legs of the SCID mice of 4-8 weeks. After about 7-8 weeks, it was found though touch that a tumor was formed, the mice were sacrificed, a paraffin section was made, and HE staining and pathological examination were carried out.

Figure 1B:
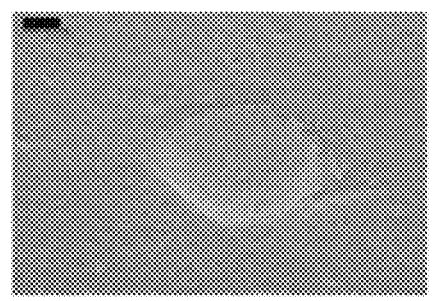
Figure 1C:
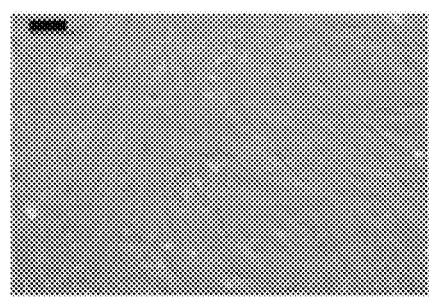
Figure 1D:
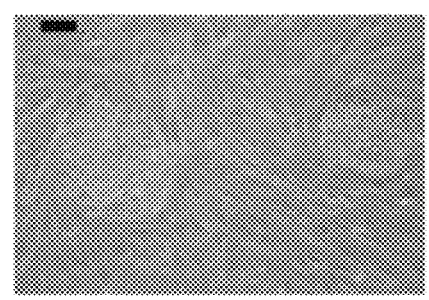
Figure 2A:
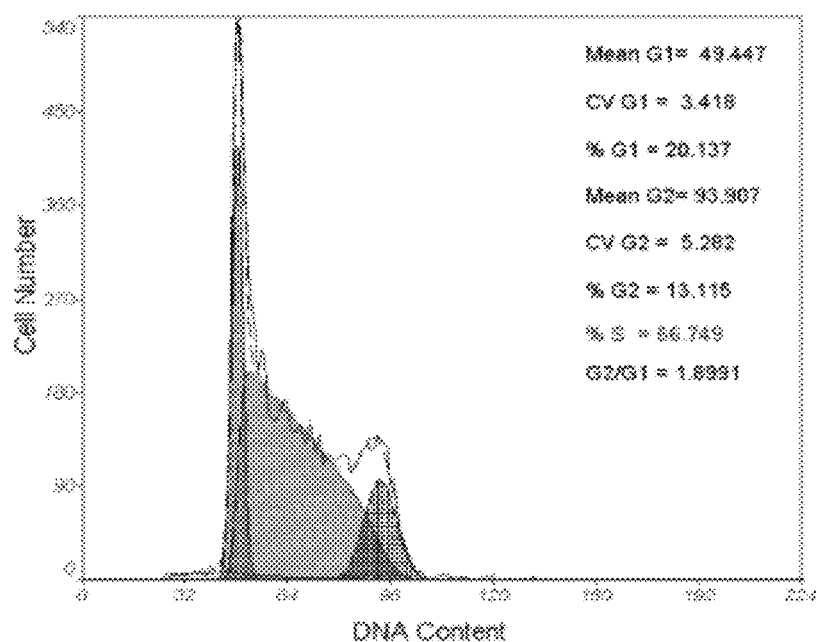
FIGS. 2A-B show DNA contents of HES cells analyzed by flow cytometry (FCM)
Figure 2B:
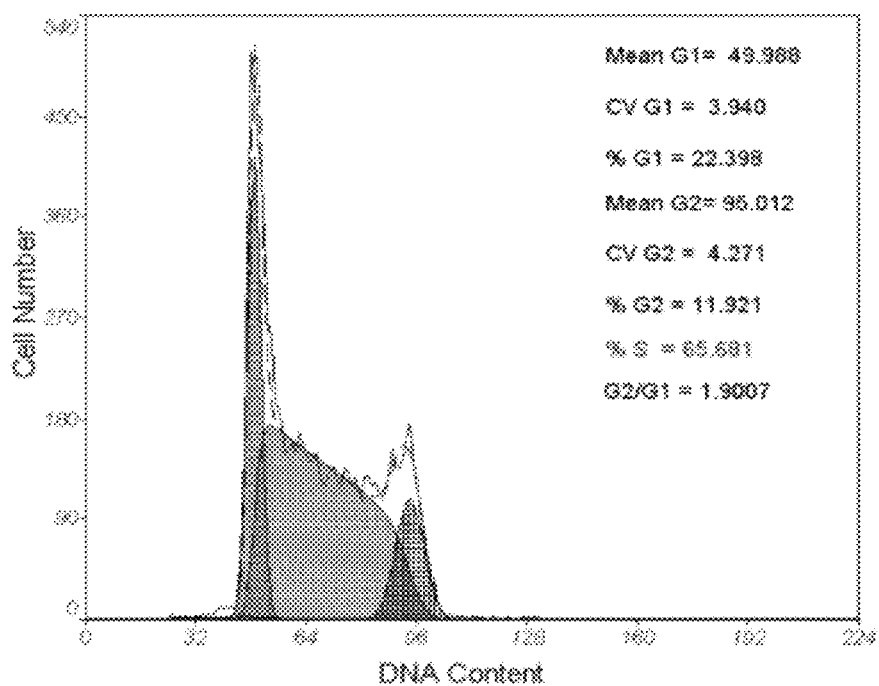

Result: it is found that the growth and proliferation rates of hHES1 on the two feeder layers have no significant difference. However, the clones grown on the human amniotic epithelial cell feeder layer is regular, dome up layer by layer like a small hill, and cannot be easily broken down by mechanical micro-desection, and relatively homogenous clones are formed after 30 passages. Differentiation easily occurs to clones on the MEF feeder layer, and irregular elliptic clones are exhibited, which are easily broken down by micro-desection (FIG. 1 shows growth of human embryonic stem cell line hHES1 on HAEC and MEF feeder layers. FIG. 1A shows the cultured human amniotic epithelial cell HAEC; FIG. 1B shows the growth of the hHES1 on the HAEC feeder layer; FIG. 1C shows the cultured MEF cells; and FIG. 1D shows the growth of the hHES1 on the MEF feeder layer). Meanwhile, difference between the DNA contents in the cell cycle of the hHES1 grown on different feeder layers is analyzed by flow cytometry (FCM), and it is found that the distribution of the G1, S, and G2 phases are similar (FIG. 2 shows DNA content of hHES1 cells analyzed by flow cytometry (FCM), in which FIG. 2A shows hHES1 on human amniotic epithelial cell feeder layer and FIG. 2B shows hHES1 on MEF feeder layer). In order to exclude the chromosome deformity that may be caused by HAEC, the change of the chromosome of hHES1 cultured on the human amniotic epithelial cell feeder layer after 20 passages is also analyzed, and the result shows that the chromosome has the normal 46XY karyotype.

Figure 3:
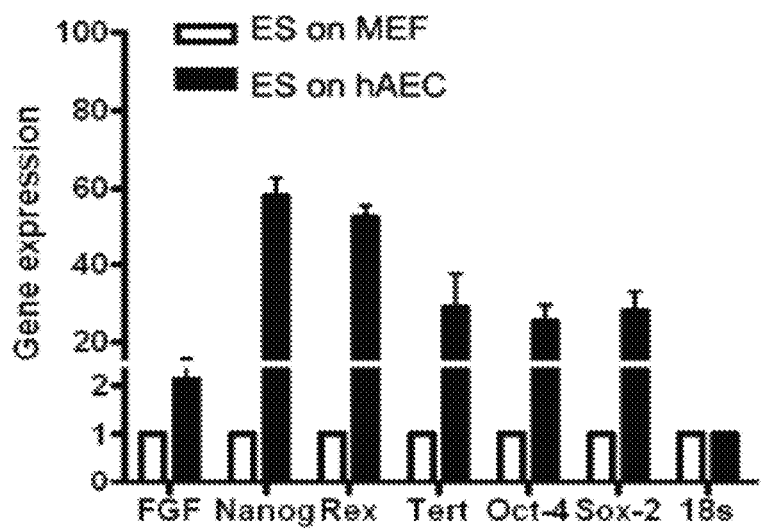
FIG. 3 shows expressions of stem cell factors of human embryonic stem cell line hHES1 growth on different feeder layer cells.
Figure 4:
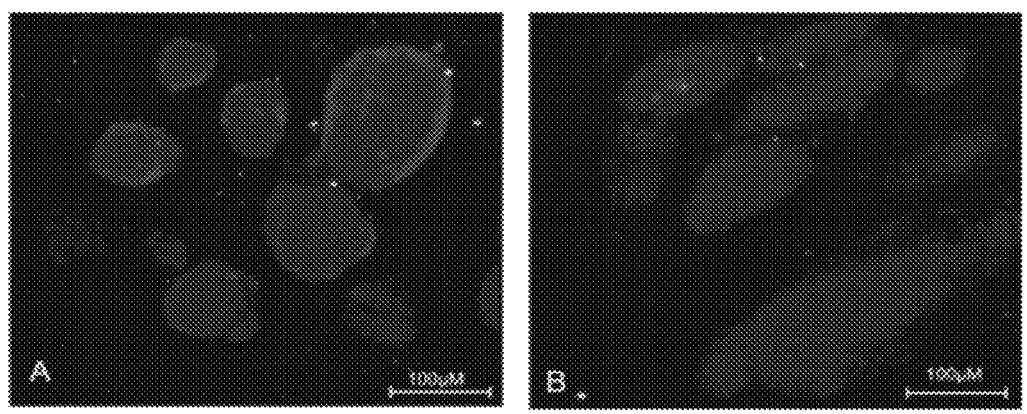
FIGS. 4A-C show teratoma stained with HE.

The qRealtime-PCR result indicates that, the hHES1 cells on the HAEC feeder layer express FGF, Nanog, Rex, TERT, OCT-4 and Sox-2 at a level that is obviously higher than that of the hHES1 cells on the MEF feeder layer (in FIG. 3, 18sRNA is an inner control and $P<0.05$). Also, immunofluorescence IF analysis of hHES1 on different feeder layers is carried out. The immunofluorescence staining (A) of Oct-4 of hHES1 clones cultured on the human amniotic epithelial cell feeder layer (A) is stronger than that of the clones on the MEF feeder layer (B) (FIG. 4).

Figure 5A:
FIG. 5 shows immunofluorescence staining of Oct-4 of hHES1.
Figure 5B:
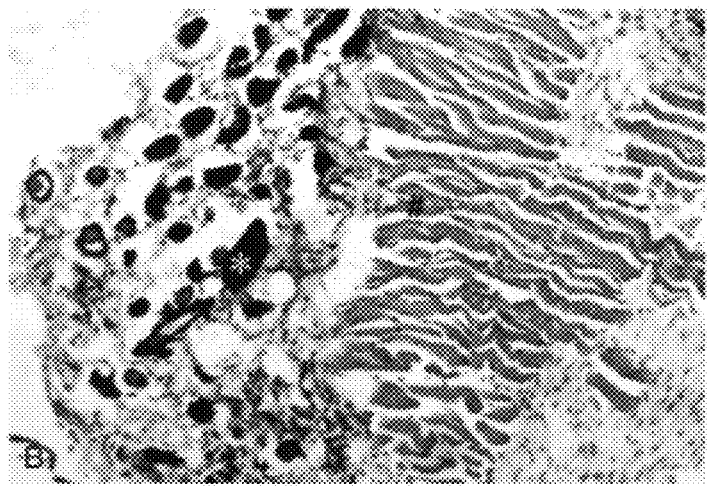
Figure 5C:
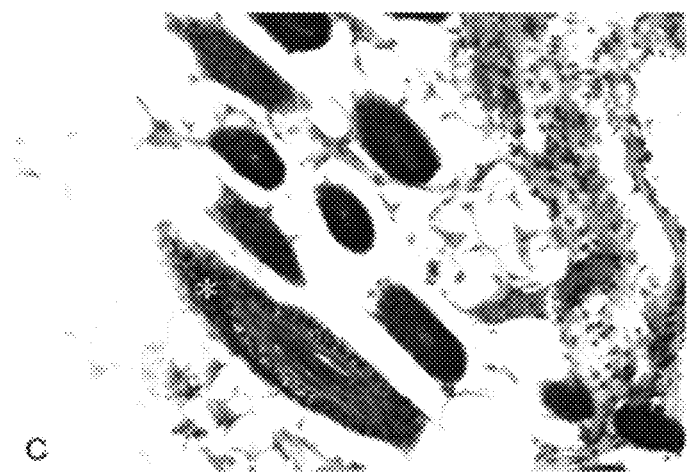

It is found through HE staining and pathological examination of the paraffin section of the tumor tissue that the teratoma formed by hHES1 cells cultured on the human amniotic epithelial cell feeder layer has three embryonic layers, and includes immature glandular tissue, muscle fiber, bone, and hair (FIG. 5A shows immature glandular tissue; FIG. 5B shows muscle fiber B; and FIG. 5C shows bone and hair).

Embodiment 4. Effects of LIF on Culture of Embryonic Stem Cells

The human amniotic epithelial cell feeder layer obtained in Embodiment 1 was used, on which the mouse embryonic stem cell line 129 was inoculated, cultured respectively in DMEM culture medium A (containing 10% FBS, 10 ng/ml bFGF, and 12 ng/ml LIF) and DMEM culture medium B (containing 10% FBS, and 10 ng/mlbFGF), and passaged 30 times. $1 \times 10^6$ 129 cells was collected and intramuscularly injected respectively into the back legs of the SCID mice of 4-8 weeks. After about 7-8 weeks, it was found though touch that a tumor was formed, the mice were sacrificed, a paraffin section was made, and HE staining and pathological examination were carried out.

Results: it is found that in the culture medium without LIF, the mouse embryonic stem cell line 129 exhibits regularly grown clones, which cannot be easily broken down by mechanical micro-desection, and relatively homogenous clones are formed after 30 passages. The mouse embryonic stem cell line 129 is tumorigenic in SCID mice, and it is found through HE staining and pathological examination of the paraffin section of the tumor tissue that the teratoma has three embryonic layers, and includes immature glandular tissue, muscle fiber, bone, and hair.

Embodiment 5. Detection of Expression of LIF in the Feeder Layer Cells

The expressions of LIF in the feeder layer cells obtained in Embodiments 1 and 2 were detected by Western blotting. Specific steps included collecting MEF and hAEC cells, homogenizing, determining the protein content by BCA kit, subjecting 20 mg protein to SDS-PAGE electrophoresis respectively, and transferring. The protein was incubated with LIF antibody (rabbit anti-human or mouse, 1:200, Wuhan Boster Biological engineering Co., Ltd.) and β-actin antibody (rabbit anti-human or mouse, 1:1000, Cell signaling, USA) for 1 hour, then incubated with a secondary antibody (1:1000, Santa Cruz Biotechnology, Santa Cruz, Calif.) for 1 hr, developed by using a Westen lightning ECL kit (PerkinElmer life science, USA), and scanned and analyzed by an imaging system (G: BOX SYNGENE, Gene company limited, Hongkong).

Figure 6:
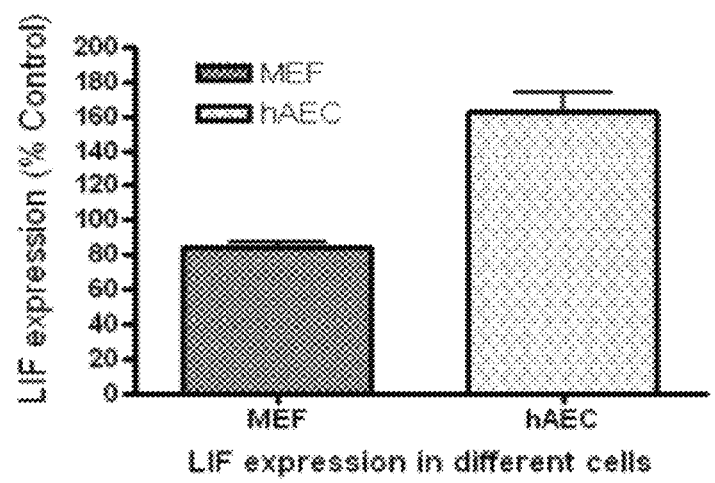
FIG. 6 shows expressions of LIF in two different feeder layer cells detected by Western blotting.

Result: the expression of LIF in HAEC is significantly higher than that in MEF (FIG. 6).

Human placenta includes three layers, i.e. amnion, chorion, and decidua. The amnion may also be referred to as fetal membrane, which is the outermost layer of the placenta, and forms an inner wall of the amniotic cavity. The amnion is a semi-transparent membrane, mainly formed by the amniotic epithelial cells in the surface ectoderm and a small amount of mesoblast cells in the basal layer, is an early embryonic development product which is closely related to the developing fetus, and provides an environment in which the embryo grows and develops. Use of the human amniotic epithelial cells as the feeder layer is reasonable. In the development of the embryo, the undifferentiated embryo is surrounded by the placenta, and the human amniotic epithelial cells derived from the placenta may have the pluripotency of early ectoderm in light of the anatomy or the histology. It is reported that the human amniotic epithelial cells further excretes a variety of growth factors, such as GF, KGF, HGF, bFGF, TGF-α, TGF-β1, TGF-β2, TGF-β3 and expresses receptors of EGF, KGF, HGF, TGF-α, TGF-β1, and TGF-β2 [Koizumi N J, Inatomi T J, Sotozono C J et al. Curr Eye Res 2000, 20:173-177].

In the present invention, it is reported that the human amniotic epithelial cells are able to support the growth of the embryonic stem cells and keep them in the undifferentiated state, so that the embryonic stem cells can keep the self-renewing and multi-directional differentiation properties of stem cells. Compared with the MEF feeder layer system, the ES clones cultured on the human amniotic epithelial cell feeder layer are not easier to differentiate, have a growth state superior to that of the ES cells cultured on the MEF feeder layer, and can express the stem cell factors such as Oct-4, Nanog, Sox-2, Rex, bFGF, and TERT at a high level, which may correlate with that HAEC can express more LIFs than MEF, in which LIFs are factors that can facilitate the self-renewing of the ES cells and inhibit the cells differentiation [Ying, Q. L., Stpyridis, M., Griffiths, D., et al. Nat Biotech 2003, 21, 183-186.].

In the stem cell culture method according to the present invention, the human amniotic epithelial cells that are not treated to lose the division ability are used, which is of great significance, since the difficulty existing in obtaining of the human tissues or the limitation caused by ethic reasons can be solved. The human amniotic epithelial cells are derived from waste placenta tissue, and thus there is no ethic problem. $1\times10^8$ HAECs can be obtained from each amnion, and the human amniotic epithelial cells do not express telomerase, and can only expand 3-4 generations, so that the proliferation is slow and the treatment with mitomycin C is not required. Therefore, the human amniotic epithelial cells are a good source of the feeder layer for culturing the human embryonic stem cells, and can solve the problem caused by animal-derived ingredients.

The scope of the present invention is not limited by specific implementations, the specific implementations are provided only for illustration of the present invention in each aspect, and equivalent methods and components also fall within the scope of the present invention. Actually, in addition to the contents described herein, various modifications of the present invention can be easily made by those skilled in the art with reference to the foregoing descriptions and accompanying drawings. The modifications also fall with the scope of the appended claims. Documents mentioned above are incorporated herein by reference in its entirety.

What is claimed is:

1. A stem cell culture method, comprising:
    a) preparing an amniotic epithelial cell feeder layer that is not treated to lose the division ability; and
    b) seeding stem cells onto the amniotic epithelial cell feeder layer, and culturing in a culture medium.

2. The stem cell culture method according to claim 1, wherein step (a) of claim 1 comprises peeling off the amnion from the placenta obtained after parturition through cesarean section, isolating amniotic epithelial cells, seeding the amniotic epithelial cells into a cell culture container, and culturing in a cell incubator at 37° C. with 5% $CO_2$.

3. The stem cell culture method according to claim 1, wherein the amniotic epithelial cells are mammalian amniotic epithelial cells.

4. The stem cell culture method according to claim 3, wherein the amniotic epithelial cells are human amniotic epithelial cells.

5. The stem cell culture method according to claim 1, wherein the amniotic epithelial cells are amniotic epithelial cells of passages $P_0$-$P_3$.

6. The stem cell culture method according to claim 1, wherein the amniotic epithelial cells are amniotic epithelial cells of passage $P_0$.

7. The stem cell culture method according to claim 1, wherein the stem cells are embryonic stem cells, embryonic germ cells, induced pluripotent stem (iPS) cells, or somatic stem cells.

8. The stem cell culture method according to claim 1, wherein the stem cells are embryonic stem cells or iPS cells.

9. The stem cell culture method according to claim 8, wherein the embryonic stem cells or iPS cells are human embryonic stem cells or human iPS cells.

10. The stem cell culture method according to claim 1, wherein the stem cells are embryonic stem cells, embryonic germ cells, or iPS cells, and in the culture medium comprises 0-12 ng/ml of LIF.

11. The stem cell culture method according to claim 1, wherein the culture medium is a serum-free culture medium or a serum-containing culture medium.

12. The stem cell culture method according to claim 11, wherein the serum is human whole serum, umbilical cord serum, animal serum, or animal embryonic serum.

* * * * *